United States Patent
Lee et al.

(10) Patent No.: US 9,406,412 B2
(45) Date of Patent: Aug. 2, 2016

(54) VARIABLE PIN-HOLE TYPE COLLIMATOR AND RADIATION IMAGING DEVICE USING THE SAME

(71) Applicant: Korea University Research and Business Foundation, Seoul (KR)

(72) Inventors: Hakjae Lee, Seoul (KR); Kisung Lee, Yongin-si (KR); Jaekeon Bae, Seoul (KR)

(73) Assignee: Korea University Research and Business Machines, Seoul (KR)

( * ) Notice: Subject to any disclaimer, the term of this patent is extended or adjusted under 35 U.S.C. 154(b) by 0 days.

(21) Appl. No.: 14/421,673

(22) PCT Filed: Jan. 7, 2014

(86) PCT No.: PCT/KR2014/000148
§ 371 (c)(1),
(2) Date: Feb. 13, 2015

(87) PCT Pub. No.: WO2014/115980
PCT Pub. Date: Jul. 31, 2014

(65) Prior Publication Data
US 2015/0235723 A1    Aug. 20, 2015

(30) Foreign Application Priority Data
Jan. 22, 2013    (KR) .......................... 10-2013-0007033

(51) Int. Cl.
*G21K 5/04*    (2006.01)
*G21K 1/04*    (2006.01)
(52) U.S. Cl.
CPC ....................................... *G21K 1/046* (2013.01)
(58) Field of Classification Search
USPC .............. 250/505.1, 516.1, 515.1, 519.1;
378/147, 148, 149, 150, 151, 152, 153
See application file for complete search history.

(56) References Cited

U.S. PATENT DOCUMENTS

2009/0001296 A1*  1/2009  Kuduvalli ................ 250/505.1
2009/0074148 A1*  3/2009  Echner .................... G21K 1/04
                                              378/152

FOREIGN PATENT DOCUMENTS

| JP | 2009-20102 A | 1/2009 |
| KR | 10-0647930 B1 | 11/2006 |
| KR | 10-2009-0093654 A | 9/2009 |
| KR | 10-2010-0074566 A | 7/2010 |
| KR | 10-1167846 B1 | 7/2012 |

OTHER PUBLICATIONS

International Search Report issued Mar. 7, 2014 in corresponding International Patent Application No. PCT/KR2014/000148 (4 pages, in Korean with English Translation).

* cited by examiner

*Primary Examiner* — Nicole Ippolito
(74) *Attorney, Agent, or Firm* — NSIP Law

(57) ABSTRACT

The present invention relates to a variable pin-hole type collimator applied to a radiation imaging device. The variable pin-hole type collimator comprises: a hole forming module having a plurality of apertures which are stacked in a direction of irradiation such that each aperture defines a penetrating-space through which radiation passes; a plurality of driving modules which are configured that each driving module varies each penetrating-space of the aperture independently; and a collimating controller to control the driving modules such that each penetrating-space of the aperture varies independently and the hole forming module forms a pin-hole through which radiation passes. Therefore, a collimator having various types can be embodied by the variation of the pin-hole shape.

4 Claims, 7 Drawing Sheets

VARIABLE PIN-HOLE TYPE COLLIMATOR AND RADIATION IMAGING DEVICE USING THE SAME

CROSS REFERENCE TO RELATED APPLICATIONS

This application is a National Phase entry of PCT Application No. PCT/KR2014/000148, filed on Jan. 7, 2014, which claims priority to Korean Patent Application No. 10-2013-0007033, filed on Jan. 22, 2013, and the entire disclosures of these applications are incorporated herein by reference for all purposes.

TECHNICAL FIELD

The present invention relates to a variable pin-hole type collimator and a radiation imaging device using the same, and in particular, to a variable pin-hole type collimator which determines a penetrating-space or a direction of radiation in a radiation imaging device such as a gamma camera or a single photon emission computed tomography (SPECT) device and a radiation imaging device using the same.

BACKGROUND ART

A radiation imaging device is one of the devices which use radioactive isotope to obtain an image and which is being widely used in the field of a nondestructive testing as well as a nuclear medicine diagnosis.

A radiation imaging device used in the field of nuclear medicine diagnosis, i.e., a gamma camera using gamma rays or a single photon emission computed tomography (SPECT) device, provides a human's functional information by using radiopharmaceutical, differently from other diagnosis devices, i.e., a magnetic resonance imaging (MRI) or a ultrasonic diagnostic device, which provide a human's structural information.

FIG. 1 represents a construction of a general gamma camera 1. The general gamma camera 1 comprises a collimator 10, a crystal scintillator, i.e., a scintillator 30 and a photomultiplier tube (PMT) 50.

The collimator 10 acts as a collimator which allows gamma rays discharged from a chaser in a body and having the same direction as the camera to pass through and blocks gamma rays having different direction. That is, the collimator 10 geometrically limits gamma rays released from a body part so that only gamma rays released from a required part enter into the scintillator 30.

Here, gamma rays which pass through the collimator 10 and reach the scintillator 30 is transformed into an electromagnetic wave having low energy, i.e., visible rays, which can be easily detected by the scintillator 30. Then, the rays are amplified in the photomultiplier tube 50 and are transformed into electric signals and the detected position or energy is stored on a computer 70 so that the image can be obtained.

Such a gamma camera is disclosed in Korean Patent No. 0841123.

A single photon emission computed tomography (SPECT) device is firstly invented by W. I. Keys in 1976 and the device for brain is developed by R. J. Jaszczak in 1979.

A single photon emission computed tomography (SPECT) device has similar operation to the gamma camera 1. It is configured such that a single photon, i.e., gamma ray, which releases radioparmaceutical is inserted into a body and a scintillation camera installed on a head rotating around the body detects at various angles that the gamma ray generated in the body penetrates the body, and tomographic cross-section images are obtained from detected signals by means of an image reconfiguration algorithm.

Therefore, like the gamma camera 1, the single photon emission computed tomography (SPECT) device also comprises a collimator 10, a scintillator 30 and a photomultiplier tube (PMT) 50.

As described above, a gamma camera 1 or a single photon emission computed tomography (SPECT) device uses a collimator through which gamma rays pass selectively and the collimator is generally made of lead or tungsten and has a fixed shape.

FIGS. 2A and 2B show a pin-hole collimator 10 of prior arts which is used in the gamma camera 1 or a single photon emission computed tomography (SPECT) device.

The pin-hole collimator 10 comprises a main body 11 constituting the entire structure and a pin-hole 12 through which gamma rays pass. As shown in FIG. 2, the pin-hole 12 is divided into the first cone region 13, a penetrating hole region 15 and the second cone region 14.

FIG. 3 shows a multiple pin-hole collimator 10a of prior arts. As shown in FIG. 3, a main body 11a has a plurality of pin-holes 12a and the plurality of pin-holes 12a are arranged vertically (see FIG. 2B) or inclined (see FIG. 7A).

Here, the shape of the pin-hole 12a is defined by the radiation angle of the first cone region 13 and the second cone region 14, the diameter and the length of the penetrating-hole region 15, etc. and the shape is determined by the size or location of the object to be taken, the size or location of the scintillator 30 and the energy of gamma rays.

But, since the shape of the pin-hole collimator 10 of prior arts is fixed as shown in FIGS. 2A, 2B, and 3, if the imaging condition such as the size or location of the object is changed, the pin-hole collimator 10 must be replaced with other collimator corresponding to the changed condition, thereby causing inconvenience.

DISCLOSURE OF THE INVENTION

Technical Problem

The present invention is invented to solve the above problems and the object of the invention is to provide a variable pin-hole type collimator which is applied to a radiation imaging device such as a gamma camera or a single photon emission computed tomography (SPECT) device and which can adjust the shape of a pin-hole to provide a collimator having various pin-hole shapes, and a radiation imaging device using the same.

Technical Solution

The object is achieved by a variable pin-hole type collimator applied to a radiation imaging device comprising: a hole forming module having a plurality of apertures which are stacked in a direction of irradiation such that each aperture defines a penetrating-space through which radiation passes; a plurality of driving modules which are configured that each driving module varies each penetrating-space of the aperture independently; and a collimating controller to control the driving modules such that each penetrating-space of the aperture varies independently and the hole forming module forms a pin-hole through which radiation passes.

Here, the penetrating-space formed by each aperture may have a circular shape or an oval shape.

Also, each aperture may be made from a radiation-shielding material.

Further, the object may be achieved by a radiation imaging device according to another embodiment of the present invention to which a variable pin-hole type collimator.

Advantageous Effect

According to the above features, the present invention is able to provide a variable pin-hole type collimator which is applied to a radiation imaging device such as a gamma camera or a single photon emission computed tomography (SPECT) device and which can adjust the shape of a pin-hole to provide a collimator having various pin-hole shapes, and a radiation imaging device using the same.

BEST MODE FOR CARRYING OUT THE INVENTION

The variable pin-hole type collimator applied to a radiation imaging device according to the present invention comprises: a hole forming module having a plurality of apertures which are stacked in a direction of irradiation such that each aperture defines a penetrating-space through which radiation passes; a plurality of driving modules which are configured that each driving module varies each penetrating-space of the aperture independently; and a collimating controller to control the driving modules such that each penetrating-space of the aperture varies independently and the hole forming module forms a pin-hole through which radiation passes.

MODE FOR CARRYING OUT THE INVENTION

Hereinafter, preferred embodiments according to the present invention will be explained in detail referring to attached drawings. A variable pin-hole type collimator according to the present invention is applied to a radiation imaging device such as a gamma camera or a single photon emission computed tomography (SPECT) device. In the present invention, a variable pin-hole type collimator is examplarily applied to a radiation imaging device for a nuclear medicine and it can also be applied to a radiation imaging device for nondestructive testing using gamma rays.

Figure 4:
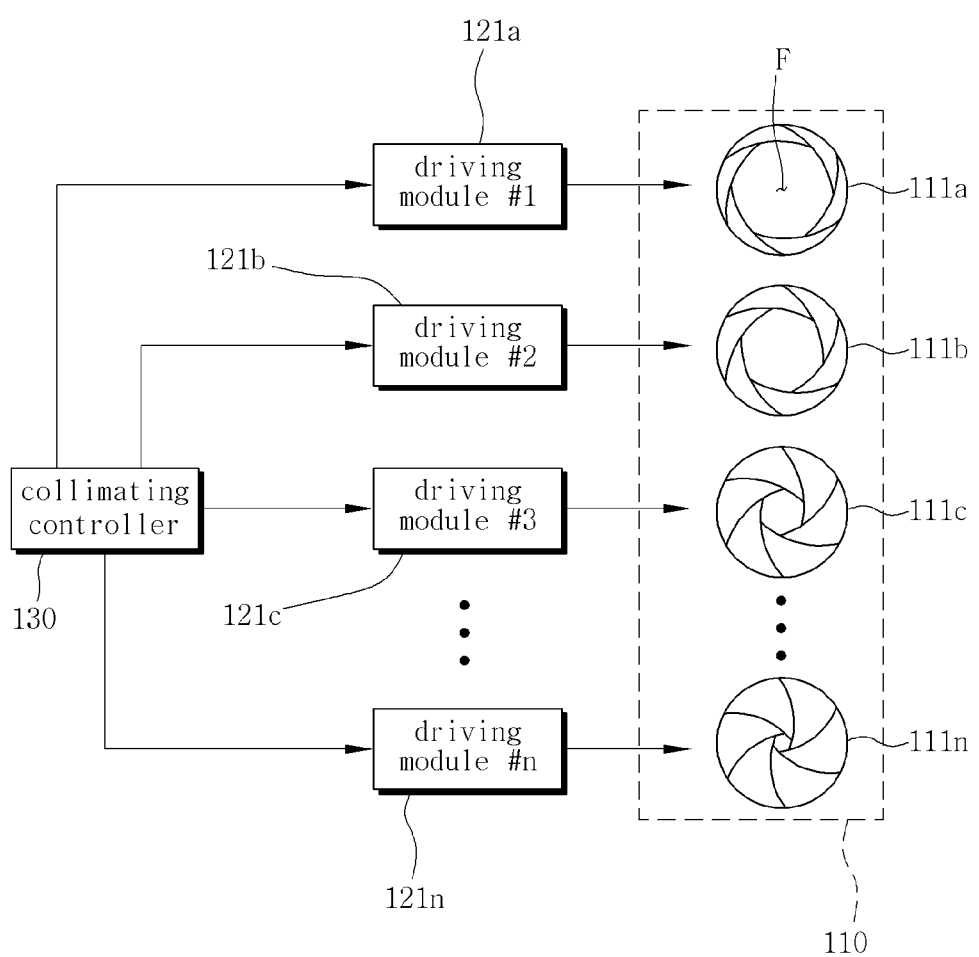
FIG. 4 shows a variable pin-hole type collimator according to the present invention.

As shown in FIG. 4, the variable pin-hole type collimator according to the present invention comprises a hole forming module 110, a plurality of driving modules 121a, 121b, 121c and 121n, and a collimating controller 130.

The module 110 for forming a pin-hole comprises a plurality of apertures 111a, 111b, 111c, 111n which are stacked in a direction of irradiation. The plurality of apertures 111a, 111b, 111c, 111n are configured to form a penetrating-space (F) through which radiation passes. Here, each aperture 111a, 111b, 111c, 111n is made of radiation-shielding material such as material including lead or tungsten.

Figure 5:
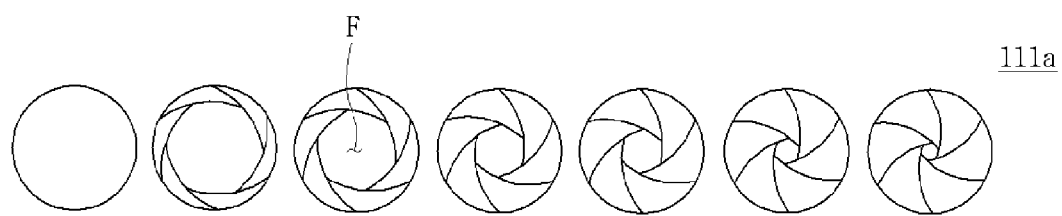
FIG. 5 represents the operation of apertures of a hole forming module according to the present invention.

Each driving module 121a, 121b, 121c, 121n varies a penetrating-space (F) of each aperture 111a, 111b, 111c, 111n, independently. The driving module 121a, 121b, 121c, 121n causes the aperture 111a, 111b, 111c, 111n to actuate, thereby varying the size of the penetrating-space (F) of each aperture 111a, 111b, 111c, 111n. FIG. 5 shows examplarily the operation of apertures 111a, 111b, 111c, 111n of a module 110 for forming a pin-hole according to the present invention and each aperture 111a, 111b, 111c, 111n is controlled by each driving module 121a, 121b, 121c, 121n to control the penetrating-space (F).

The collimating controller 130 controls the plurality of driving modules 121a, 121b, 121c, 121n such that the penetrating-space (F) of each aperture 111a, 111b, 111c, 111n varies independently. In detail, the collimating controller 130 controls the plurality of driving modules 121a, 121b, 121c, 121n in such a manner that the penetrating-space (F) of each aperture 111a, 111b, 111c, 111n varies independently, resulting in that the module 110 for forming a pin-hole generates a pin-hole 113, 114, 115 through which radiation passes.

Figure 6:
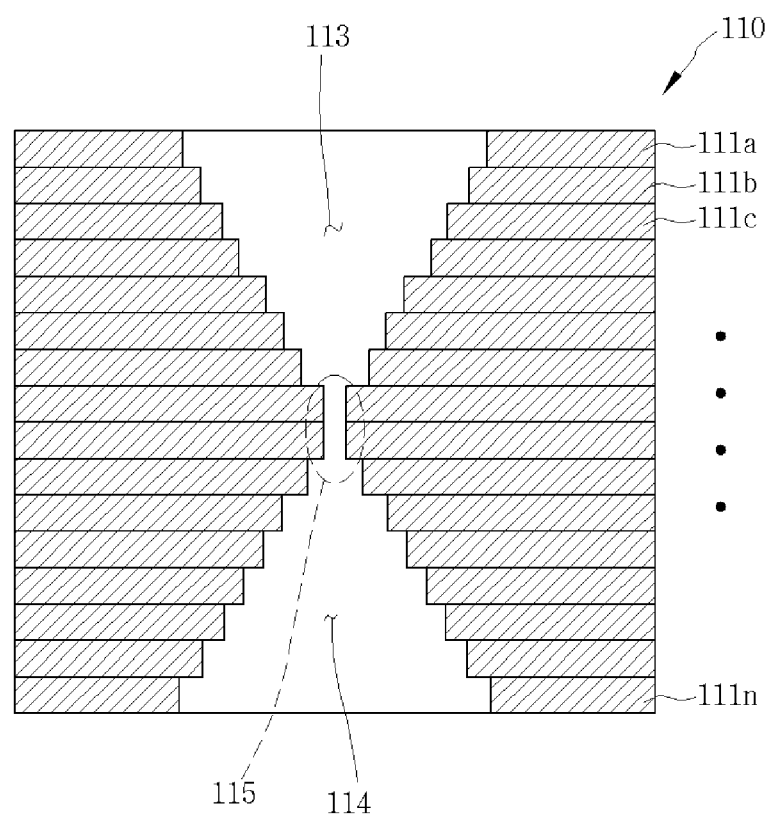
FIGS. 6, 7A, and 7B explain the operation of a hole forming module of a variable pin-hole type collimator according to the present invention.
Figure 7A:
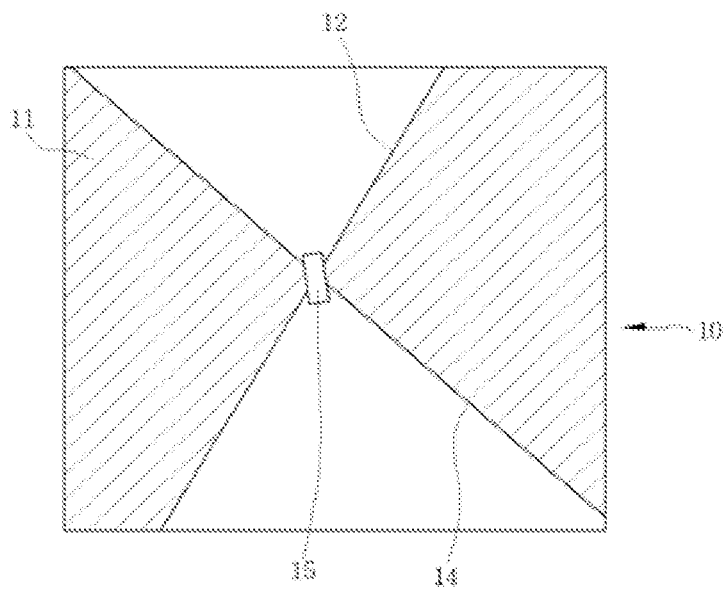
Figure 7B:
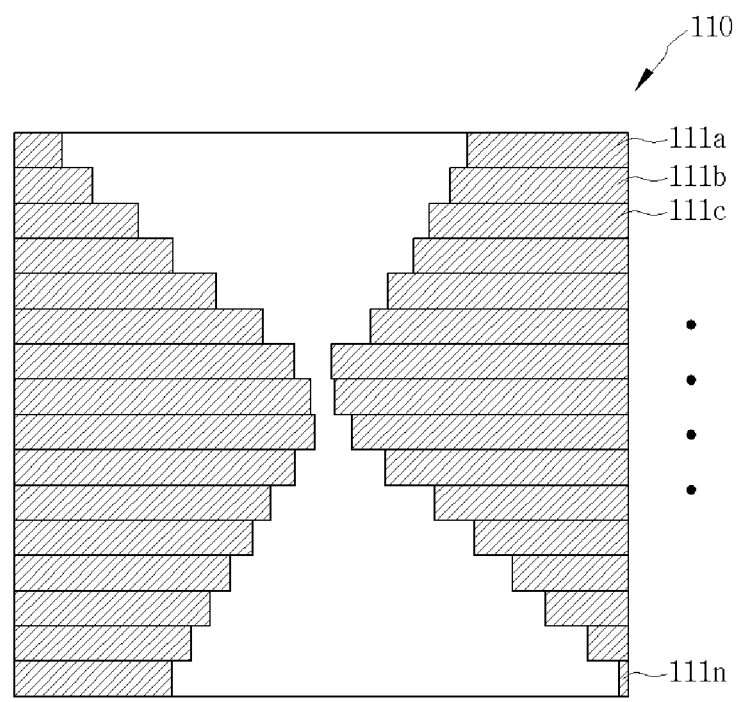

FIGS. 6, 7A, and 7B explain the operation of a module 110 for forming a pin-hole of a variable pin-hole type collimator according to the present invention and shows a cross-sectional view of the module 110 for forming a pin-hole in a radiation-penetrating direction.

Referring to FIGS. 6, 7A, and 7B, the module 110 for forming a pin-hole is configured such that a plurality of apertures 111a, 111b, 111c, 111n are stacked in a direction of irradiation, as described above. Here, if the penetrating-space (F) of each aperture 111a, 111b, 111c, 111n varies independently by the actuation of each driving module 121a, 121b, 121c, 121n, the shape of the cross-section in a direction of irradiation can be controlled as can be seen in FIGS. 6, 7A and 7B.

Figure 1:
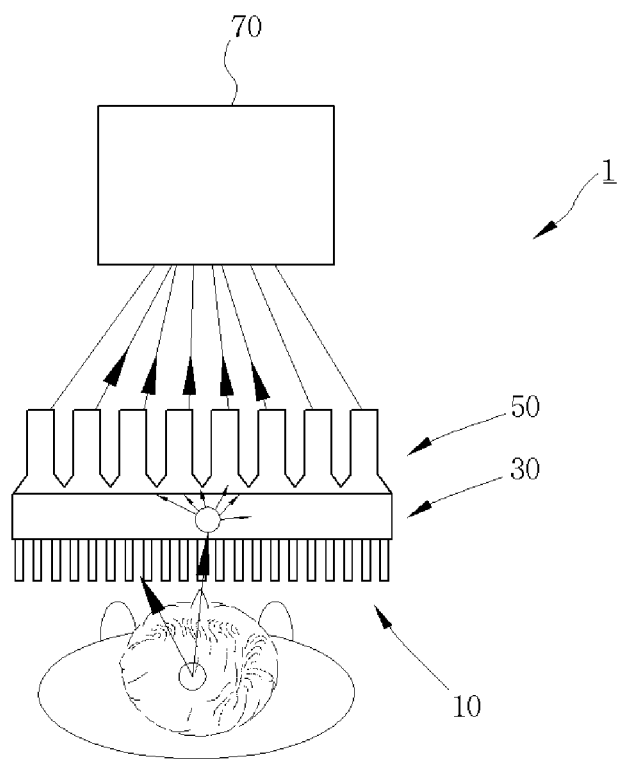
FIG. 1 shows a general gamma camera.
Figure 2A:
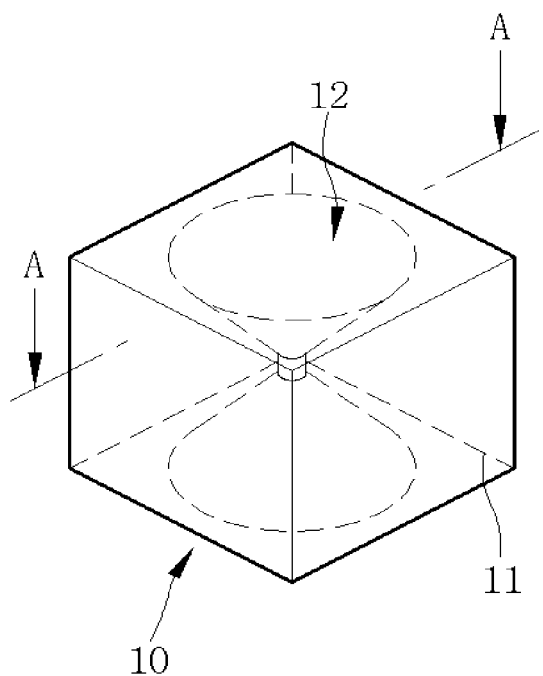
FIGS. 2A and 2B show a pin-hole collimator of prior arts.
Figure 2B:
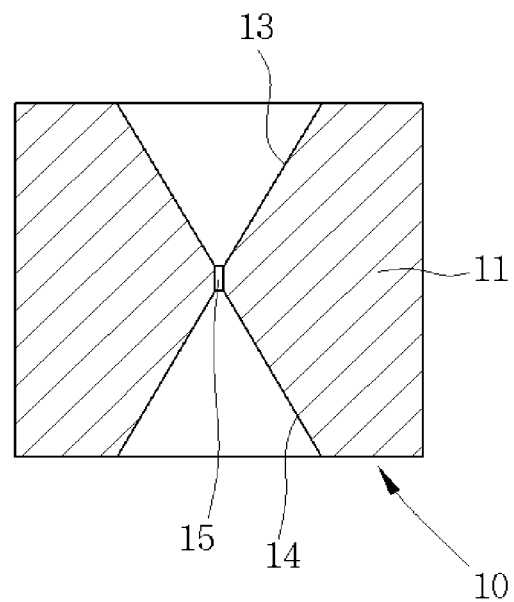

FIG. 6 shows that the prior-art pin-hole collimator 10 in FIG. 2B is embodied by the control of the penetrating-space (F) of apertures 111a, 111b, 111c, 111n. The shape of the pin-hole collimator 10 in FIG. 2B can be embodied in such a manner that the first cone region 113 is formed by decreasing the size of the penetrating-space (F) of the apertures 111a, 111b, 111c, 111n gradually from the top, a penetrating-hole region 115 is formed by means of the intermediate apertures 111a, 111b, 111c, 111d, and then the second cone region 115 is formed by increasing the size of the penetrating-space (F) of the apertures 111a, 111b, 111c, 111n gradually from the penetrating-hole region 115.

Figure 3:
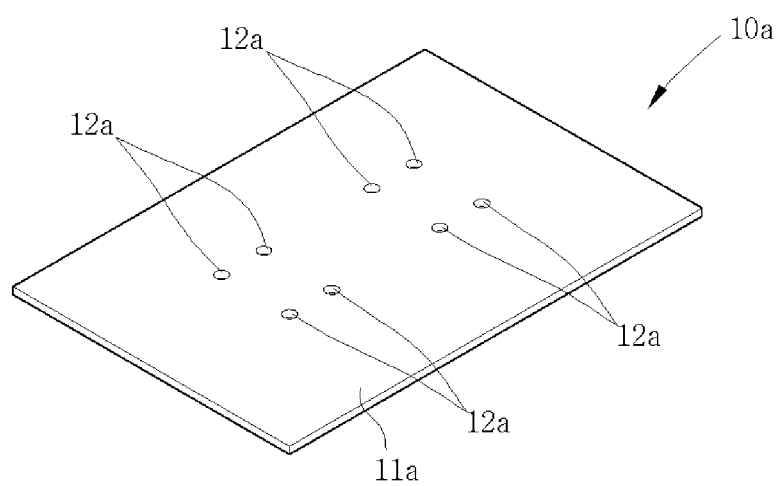
FIG. 3 shows a multiple pin-hole collimator of prior arts.

FIG. 7A shows a cross section of the pin-hole collimator 10 of prior arts and represents an application of a multiple pin-hole collimator 10a in FIG. 3. As shown in FIG. 7A, pin-holes 113, 114, 115 are inclined at an angle to a vertical direction.

The pin-hole 12 of the pin-hole collimator 10 in FIG. 7A can be embodied by the module 110 for forming a pin-hole of the variable pin-hole type collimator according to the present invention as shown in FIG. 7B.

Here, the penetrating-space (F) formed by each aperture 111a, 111b, 111c, 111d constituting the module 110 for forming a pin-hole may be configured to have a elliptic or oval shape. By this, the shape of the pin-hole as shown in FIG. 7B can be realized more easily.

According to the above arrangement, the variable pin-hole type collimator according to the present invention is able to have various shapes of the pin-holes 113, 114, 115 and therefore it is able to adapt itself to the changes in the size or location of the object to be taken, the size or location of the Scintillator, energy of gamma rays, etc. without replacement of the pin-hole collimator 10. Also, the image taken by the control of the module 10 for forming a pin-hole can be enlarged or reduced without replacement of the pin-hole collimator 10.

In case of the multiple pin-hole collimator 10a, the size of the light detector must be also enlarged according to FOV of the pin-holes 113, 114, 115. However, the present invention is able to take the function of the multiple pin-hole collimator 10a of prior arts, while maintaining the size of the photomultiplier tube (PMT).

Further, the present invention can adapt itself to gamma rays having various energy in the range of low energy to high energy and can take image of various isotopes without replacement of the pin-hole collimator 10.

It will be appreciated that although some embodiments are illustrated and described, various modifications or variations can be made without departing from the scope and spirit of the invention. The scope of the present invention may be determined by the accompanying claims and may comprise their equivalents.

LIST OF REFERENCE NUMERALS

110: hole forming module
111a, 111b, 111c, 111n: aperture
121a, 121b, 121c, 121n: driving module
130: collimator controller

INDUSTRIAL APPLICABILITY

A variable pin-hole type collimator and a radiation imaging device using the same according to the present invention, can be used to determine a penetrating-space or a direction of radiation in a radiation imaging device such as a gamma camera or a single photon emission computed tomography (SPECT) device.

The invention claimed is:

1. A variable pin-hole type collimator applied to a radiation imaging device comprising:
    a hole forming module having a plurality of apertures which are stacked in a direction of irradiation such that each aperture defines a penetrating-space through which radiation passes;
    a plurality of driving modules which are configured such that each driving module varies each penetrating-space of the aperture independently; and
    a collimating controller to control the driving modules such that each penetrating-space of the aperture varies independently and the hole forming module forms a pin-hole, which is divided into a first cone region, a penetrating hole region and a second cone region, through which radiation passes.

2. The variable pin-hole type collimator according to claim 1, wherein the penetrating-space formed by each aperture has a circular shape or an oval shape.

3. The variable pin-hole type collimator according to claim 1, wherein each aperture is made from a radiation-shielding material.

4. A radiation imaging device to which a variable pin-hole type collimator according to claim 1 is applied.

* * * * *